(12) United States Patent
Bartolini et al.

(10) Patent No.: US 7,473,668 B2
(45) Date of Patent: Jan. 6, 2009

(54) CATALYTIC COMPOSITION FOR THE DEHYDROGENATION OF ALKYLAROMATIC HYDROCARBONS

(75) Inventors: Andrea Bartolini, San Giuliano Milanese-Milan (IT); Domenico Sanfilippo, Paullo-Milan (IT); Rodolfo Iezzi, San Donato Milanese-Milan (IT)

(73) Assignee: Snamprogetti S.p.A., San Donato Milanese (IT)

( * ) Notice: Subject to any disclaimer, the term of this patent is extended or adjusted under 35 U.S.C. 154(b) by 853 days.

(21) Appl. No.: 10/494,523

(22) PCT Filed: Dec. 18, 2002

(86) PCT No.: PCT/EP02/14816

§ 371 (c)(1),
(2), (4) Date: May 14, 2004

(87) PCT Pub. No.: WO03/053567

PCT Pub. Date: Jul. 3, 2003

(65) Prior Publication Data

US 2004/0259727 A1 Dec. 23, 2004

(30) Foreign Application Priority Data

Dec. 20, 2001 (IT) .................... MI2001A2709

(51) Int. Cl.
*B01J 23/00* (2006.01)
*B01J 21/00* (2006.01)
*B01J 20/00* (2006.01)

(52) U.S. Cl. ............... 502/327; 502/263; 502/324; 502/328; 502/330; 502/332; 502/334; 502/339; 502/341; 502/344; 502/355; 502/415; 502/439

(58) Field of Classification Search ............ 502/263, 502/327, 328, 330, 332, 334, 339, 355, 415, 502/439, 324, 341, 344

See application file for complete search history.

(56) References Cited

U.S. PATENT DOCUMENTS

| 4,158,737 | A | * | 6/1979 | Bartsch ............... 560/245 |
|---|---|---|---|---|
| 4,211,672 | A | * | 7/1980 | Sonetaka et al. ......... 502/66 |
| 4,238,366 | A | * | 12/1980 | Antos ............... 502/230 |
| 4,353,815 | A | * | 10/1982 | Antos ............... 502/328 |
| 4,636,314 | A | * | 1/1987 | Beuhler et al. ....... 210/500.25 |
| 4,757,045 | A | * | 7/1988 | Turner et al. ........... 502/252 |
| 5,145,826 | A | * | 9/1992 | Hirschberg et al. ...... 502/262 |
| 5,308,822 | A | * | 5/1994 | Iezzi et al. ............ 502/243 |
| 5,371,306 | A | | 12/1994 | Woo et al. |
| 5,414,182 | A | * | 5/1995 | Iezzi et al. ............ 585/661 |
| 5,600,000 | A | * | 2/1997 | King ............... 564/480 |
| 5,750,790 | A | * | 5/1998 | King ............... 564/469 |
| 5,772,898 | A | | 6/1998 | Lewis |
| 5,965,481 | A | * | 10/1999 | Durand et al. .......... 502/304 |
| 5,990,038 | A | * | 11/1999 | Suga et al. ............ 502/303 |
| 6,913,739 | B2 | * | 7/2005 | Shore et al. ............ 423/247 |

FOREIGN PATENT DOCUMENTS

| EP | 0885654 | 12/1998 |
|---|---|---|
| FR | 2735395 | 12/1996 |
| JP | 8150338 | 6/1996 |

* cited by examiner

*Primary Examiner*—Cam N. Nguyen
(74) *Attorney, Agent, or Firm*—Oblon, Spivak, McClelland, Maier & Neustadt, P.C.

(57) ABSTRACT

Process for the catalytic dehydrogenation of alkylaromatic hydrocarbons optionally mixed with ethane which comprises: A) dehydrogenating the hydrocarbon stream, optionally mixed with an inert gas, in a fluid bed reactor in the presence of a catalytic composition based on gallium and manganese supported on alumina modified with silica, at a temperature ranging from 400 to 700° C., at a total pressure ranging from 0.1 to 3 ata and with a GHSV (Gas Hourly Space Velocity) ranging from 50 to 10,000 $h^{-1}$; and B) regenerating and heating the catalyst, by means of the catalytic oxidation of a fuel, in a fluid bed regenerator at a temperature higher than 400° C.

22 Claims, No Drawings

CATALYTIC COMPOSITION FOR THE DEHYDROGENATION OF ALKYLAROMATIC HYDROCARBONS

CROSS REFERENCE TO RELATED APPLICATION

This application is a 371 of PCT/EP02/014816, filed Dec. 18, 2002 and claims priority to Italian Patent Application No. MI2001A002709, filed Dec. 20, 2001.

The present invention relates to a catalytic composition for the dehydrogenation of alkylaromatic hydrocarbons.

More specifically, the present invention relates to a catalytic composition for the dehydrogenation of alkylaromatic hydrocarbons optionally in the presence of an inert or hydrocarbon diluent.

Even more specifically, the present invention relates to a catalytic composition for the dehydrogenation of ethylbenzene optionally diluted in an inert product or ethane.

Processes for the dehydrogenation of alkylaromatic hydrocarbons are known. U.S. Pat. No. 6,031,143, for example, describes a process for the contemporaneous dehydrogenation of ethylbenzene and ethane in the presence of a catalytic system consisting of an inorganic carrier, such as alumina, on which various metals have been impregnated with the purpose of activating the chemical reactions involved in the process.

Other examples of processes for the dehydrogenation of alkylaromatic hydrocarbons are provided in European patent 885,654 and in international patent application PCT 00/09196.

In these documents, the dehydrogenation of the alkylaromatic hydrocarbon, in particular ethylbenzene to styrene, is carried out in a unit consisting of a reactor/regenerator system both operating under fluid bed conditions. In this kind of system, the dehydrogenation unit comprises a first fluid bed dehydrogenation reactor and a second regeneration reactor of the catalyst containing coke. The latter is removed in continuous from the bottom of the first reactor and is fed to the head of the second reactor where it is maintained under fluid conditions by a mixture of fuel gas, for example methane, and preheated air. In this way, the solid slowly descends in countercurrent with the gaseous stream which rises and during this slow descent it is regenerated as the carbonaceous residues are burnt. The passage of the catalyst from one reactor to the other is guaranteed by a carrier gas such as air or nitrogen, for example.

The optimum temperature conditions in the regenerator range from 500 to 700° C. and are maintained as a result of the catalytic oxidation of fuel gas (for example methane). The catalytic system therefore comprises metals active both in the dehydrogenation reaction, such as gallium or chromium combined with an alkaline metal such as potassium, and in the catalytic oxidation of methane, such as platinum.

As often happens in heterogeneous catalytic systems containing multiple active components, the activity of the single components can decrease with different times. In the case of dehydrogenation, when operating with the reactor/regenerator system, the catalytic activity of the platinum is considerably lower than that of other metals such as gallium or chromium. This fact has a certain influence on the economy of dehydrogenation processes as the substitution of the platinum catalyst also implies that of the other metal catalysts, still active, as they are all impregnated on the same carrier.

The Applicant has now found that manganese, either alone or combined with platinum itself, if impregnated on an inorganic carrier such as that described in the known art, together with other dehydrogenation catalysts, is not only active in the catalytic oxidation of methane but also has a duration comparable with that of metals active in catalytic dehydrogenation.

The object of the present invention therefore relates to a catalytic composition for the dehydrogenation of alkylaromatic hydrocarbons optionally mixed with ethane, in a reactor/regenerator system, which comprises:

a) a carrier consisting of alumina in delta phase or in theta phase or in a mixture of delta+theta, theta+alpha or delta+theta+alpha phase, modified with silica, and having a surface area lower than 150 m$^2$/g, determined with the BET method;
b) 0.1-35% by weight of gallium expressed as $Ga_2O_3$;
c) 0.01-5% by weight of manganese expressed as $Mn_2O_3$;
d) 0-100 ppm by weight of platinum;
e) 0.05-4% by weight of an oxide of an alkaline or earth-alkaline metal;

the percentages being calculated with respect to the total of the composition.

According to a preferred embodiment of the present invention, the catalytic composition for the dehydrogenation of alkylaromatic hydrocarbons optionally mixed with ethane, in a reactor/regenerator system, comprises:

a) a carrier consisting of alumina in delta phase or in theta phase or in a mixture of delta+theta, theta+alpha or delta+theta+alpha phase, modified with silica, and having a surface area lower than 150 m$^2$/g, determined with the BET method;
b) 0.2-3.8% by weight of $Ga_2O_3$;
c) 0.15-1.5% by weight of manganese expressed as $Mn_2O_3$;
d) 5-90 ppm by weight of platinum;
e) 0.1-3% by weight of an oxide of an alkaline or earth-alkaline metal;

the percentages being calculated with respect to the total of the composition.

The process for preparing the catalytic system described above can be substantially carried out by means of the following steps:

preparing one or more solutions of the components to be supported;

dispersing the solutions on the alumina carrier modified with silica;

drying the impregnated carrier; and calcining the dried carrier at a temperature ranging from 500 to 900° C.;

optionally repeating the previous steps one or twice.

In the preparation of the catalysts object of the present invention, the modified alumina carrier is in the form of particles classified as belonging to group A according to Geldart (Gas Fluidization Technology, D. Geldart, John Wiley & Sons).

The dispersion of the catalyst components on the carrier can be carried out according to the conventional techniques, such as impregnation, ion exchange, "vapour deposition" or surface adsorption. The incipient wetness impregnation technique is preferably used.

The catalyst, object of the present invention, has also proved to be surprisingly effective in the form of mechanical mixtures of the respective supported active metal components. A further object of the present invention therefore relates to a catalytic composition for the dehydrogenation of alkylaromatic hydrocarbons optionally mixed with ethane, in a reactor/regenerator system, comprising a mechanical mixture of:

i) 70-99.5% by weight, preferably from 80 to 95%, of a first active phase essentially consisting of a solid carrier based on alumina in delta phase or in theta phase or in a mixture of delta+theta, theta+alpha or delta+theta+alpha phase, modified with silica, and having a surface area lower than 150 m$^2$/g, determined with the BET method, gallium, expressed as $Ga_2O_3$, and an oxide of an alkaline or earth-alkaline metal supported on alumina, in quantities, calculated with respect to the total, ranging from 0.1 to 35% by weight and 0.05 to 4% by weight, respectively;

ii) 0.5-30% by weight, preferably from 5 to 20%, of a second active phase essentially consisting of a solid carrier based on alumina in delta phase or in theta phase or in a mixture of delta+theta, theta+alpha or delta+theta+alpha phase, modified with silica, and having a surface area lower than 150 m$^2$/g, determined with the BET method, modified with manganese, expressed as $Mn_2O_3$, platinum and an oxide of an alkaline or earth-alkaline metal supported on alumina, in quantities, calculated with respect to the total, ranging from 0.1 to 10% by weight, 0 to 1000 ppm by weight, and 0.025 to 3.95% by weight, respectively.

The preferred catalytic mechanical mixture is that in which the quantity of gallium ranges from 0.2 to 3.8% by weight, the quantity of manganese ranges from 0.15 to 1.5% by weight, the quantity of platinum ranges from 5 to 50 ppm by weight and the total quantity of alkaline or earth-alkaline metal oxide ranges from 0.1-3% by weight.

A further object of the present invention relates to a catalytic composition for the dehydrogenation of alkylaromatic hydrocarbons optionally mixed with ethane, in a reactor/regenerator system, which comprises a mechanical mixture of:

i) 70-99.5% by weight, preferably from 80 to 95%, of a first active phase essentially consisting of a solid carrier based on alumina in delta phase or in theta phase or in a mixture of delta+theta, theta+alpha or delta+theta+alpha phase, modified with silica, and having a surface area lower than 150 m$^2$/g, determined with the BET method, gallium, expressed as $Ga_2O_3$, and an oxide of an alkaline or earth-alkaline metal supported on alumina, in quantities, calculated with respect to the total, ranging from 0.1 to 35% by weight and 0.025 to 2% by weight, respectively;

ii) 0-30% by weight, preferably from 5 to 20%, of a second active phase essentially consisting of a solid carrier based on alumina in delta phase or in theta phase or in a mixture of delta+theta, theta+alpha or delta+theta+alpha phase, modified with silica, and having a surface area lower than 150 m$^2$/g, determined with the BET method, manganese, expressed as $Mn_2O_3$, and an oxide of an alkaline or earth-alkaline metal supported on alumina, in quantities, calculated with respect to the total, ranging from 0.1 to 10% by weight and 0.025 to 3.95% by weight, respectively;

iii) 0-30% by weight, preferably from 5 to 20%, of a third active phase essentially consisting of a solid carrier based on alumina in delta phase or in theta phase or in a mixture of delta+theta, theta+alpha or delta+theta+alpha phase, modified with silica, and having a surface area lower than 150 m$^2$/g, determined with the BET method, platinum, and an oxide of an alkaline or earth-alkaline metal supported on alumina, in quantities, calculated with respect to the total, ranging from 5 to 1000 ppm by weight and 0.025 to 3.95% by weight, respectively.

In this second catalytic mechanical mixture, the quantity of gallium can range from 0.2 to 3.8% by weight, the quantity of manganese can range from 0.15-1.5% by weight, the quantity of platinum from 5 to 50 ppm by weight and the total quantity of alkaline or earth-alkaline metal oxide ranges from 0.1-3% by weight.

In the catalytic composition, object of the present invention, whether it consists of a single carrier on which the active metals are impregnated or various carriers impregnated separately and then mechanically mixed, the alumina carrier is modified with 0.08-5% by weight of silica whereas the preferred alkaline or earth-alkaline metal is potassium or magnesium.

Also in the case of a catalytic composition consisting of a mechanical mixture of carriers impregnated separately with active metals, the alumina is used in the form of particles which are such as to be classified as belonging to group A according to Geldart (Gas Fluidization Technology, D. Geldart, John Wiley & Sons).

The catalytic system, object of the present invention, either as a single active phase or as a mechanical mixture of various active phases, can be used in a process for the catalytic dehydrogenation of alkylaromatic hydrocarbons optionally mixed with ethane, in a reactor/regenerator system which comprises:

A) dehydrogenating the hydrocarbon stream, optionally mixed with an inert gas, in a fluid bed reactor in the presence of a catalytic composition according to any of the claims, at a temperature ranging from 400 to 650° C., at a total pressure ranging from 0.1 to 3 ata and with a GHSV (Gas Hourly Space Velocity) ranging from 50 to 10,000 Nl/h·l$_{cat.}$; and B) regenerating and heating the catalyst, by means of catalytic combustion, in a fluid bed regenerator at a temperature higher than 500° C.

The preferred alkylaromatic hydrocarbon is generally ethylbenzene.

Nitrogen, methane, hydrogen, carbon dioxide and noble gases can be used as inert gas, preferably nitrogen and methane, with a volume ratio inert gas/hydrocarbon stream ranging from 1 to 10, preferably from 2 to 6.

In the reactor/regenerator system, the catalyst in a fluidized state circulates continuously between the two apparatuses, allowing the process to be carried out in continuous.

The heat necessary for the dehydrogenation is supplied by the regenerated catalyst which reaches the reactor at a temperature higher than the reaction temperature. The catalyst is maintained in a fluidized state in the reactor by the reagent mixture, including the optional inert gas.

The reacted gas, after passing through a system of cyclones or another separation system of the powders, leaves the reactor from above. The gas can be subsequently sent to a heat exchanger for the pre-heating of the feeding and then to the separation section where the dehydrogenation products are separated from the non-reacted charge, which is recycled. The reaction by-products can be used as fuel gas in the regenerator.

In the dehydrogenation reactor, the catalyst in a fluidized state moves in countercurrent with respect to the gaseous phase. It enters the catalytic bed from above and leaves the reactor from below, passing by gravity into a desorption zone so that the shifted, desorbed gas re-enters the reactor, avoiding the loss of reagents or products.

In the fluid bed reactor, the dehydrogenation reaction of step (A) is carried out at a temperature ranging from 450 to 650° C., at atmospheric pressure or a slightly higher value, at a GHSV ranging from 100 to 1,000 Nl/h·l$_{cat.}$, preferably from 150 to 400 Nl/h·l$_{cat}$, and with residence times of the catalyst ranging from 5 to 30 minutes, preferably from 10 to 15 minutes.

Appropriate internal devices such as grids or cylindrical bars, capable of preventing the re-mixing of the gas and catalyst, can be horizontally arranged inside the dehydrogenation reactor, so that the stream of gas inside the reactor approaches a plug flow. The use of these internal devices allows the conversion and selectivity of the hydrocarbons to be maximized.

The catalyst is subsequently sent to the regenerator by gravity or through a pneumatic conveying system consisting of:

a conveying line with at least one area in which the catalyst moves downwards optionally with a feeding of gas (nitrogen or methane); and an area in which the catalyst moves upwards, until it reaches the bed of the regenerator, by the introduction of gas.

The regeneration of the catalyst is carried out by the combustion of the carbonaceous residues with air or oxygen, whereas its heating is effected by catalytic combustion, using methane, a fuel gas or by-products of the dehydrogenation reaction, up to a temperature higher than the maximum reaction value.

The movement of the gas and solid takes place in countercurrent also in the regenerator. Air, oxygen or air diluted in nitrogen is charged into the catalytic bed whereas the fuel gas is charged at different heights along the bed.

The gas leaving the regenerator, essentially consisting of nitrogen and combustion products, passes through a system of cyclones, or other system, situated in the upper part of the apparatus, to separate the entrained powders.

The regeneration of the catalyst in step (B) is effected at a higher temperature with respect to the dehydrogenation temperature, at atmospheric pressure or a slightly higher value, a GHSV ranging from 100 to 1,000 Nl/h·l$_{cat}$ and with a residence time of the catalyst ranging from 5 to 120 minutes. In particular, the regeneration temperature ranges from 500 to 700° C. and the residence time ranges from 20 to 40 minutes.

The regenerated and heated catalyst is conveyed to the reactor by means of a pneumatic system analogous to that described for the conveying from the reactor to the regenerator.

The dehydrogenation process, object of the present invention, is particularly suitable for the contemporaneous dehydrogenation of ethane and ethylbenzene. In this case, in the dehydrogenation step (A), an ethylbenzene-ethane mixture is fed to the reactor, obtaining the contemporaneous dehydrogenation of these to give styrene and ethylene. The styrene is then separated and the ethylene, together with a stream of benzene, is fed to an alkylation unit to produce ethylbenzene.

Some illustrative and non-limiting examples are provided for a better understanding of the present invention and for its embodiment.

The catalytic combustion tests of the following examples are carried out in a quartz fluid bed reactor with porous septa also made of quartz, heated by means of external electrical resistances.

The fuel (methane) and combustion supporter (air) reach the catalytic bed from two different distributors both at the base of the catalytic bed, in order to avoid any contact before entering the catalytic bed itself. The overall composition of the feeding is 3% by volume of methane, the remainder consisting of air.

The effluent of the reactor is cooled to room temperature and the condensed water separated from the gas component which is collected in a multilayered sampling bag.

The contents of the bag are finally analyzed by means of gaschromatography to determine the CO, $CO_2$, $CH_4$, $O_2$, $N_2$ content.

The conversion of methane is finally calculated as follows:

$$\text{Conv. } CH_4 = 1 - (\% \ CH_4 / (\% \ CH_4 + \% \ CO + \% \ CO_2))$$

wherein:

% $CH_4$=concentration of methane (% Vol.) in the sample collected;

% CO=concentration of carbon monoxide (% Vol.) in the sample collected;

% $CO_2$=concentration of carbon dioxide (% Vol.) in the sample collected.

The catalytic dehydrogenation tests are carried out with analogous equipment and procedures to those described in European patent 905,112.

EXAMPLE 1

Comparative—Non-Promoted Carrier

A microspheroidal pseudobohemite is prepared to which silica (1.2% by weight) has been added, with a particle diameter ranging from 5 to 300 μm, by the spray drying of an alumina hydrate sol and Ludox silica.

A sample of the pseudobohemite is calcined at 450° C. for 1 hour, and then at 1140° C. for 4 hours in a stream of air saturated with vapor. The product obtained has a specific surface of 74 m$^2$/g, a porosity of 0.23 cc/g and consists of delta, theta and alpha transition aluminas.

An aliquot of this material is tested in a catalytic combustion test. The results are indicated in Table 1, from which it can be deduced that the catalytic performance is unsatisfactory.

EXAMPLE 2

Reference—Catalyst Based on Gallium Alone, Without Promoters 150 g of microspheroidal alumina prepared as described in Example 1 are impregnated, by means of the "incipient wetness" procedure, with 35 ml of an aqueous solution containing 24.5 g of a solution of Ga(NO$_3$)$_3$ (10.71% by weight of Ga) and 14.3 g of a solution of KNO$_3$ (6.445% by weight of K), the remaining consisting of deionized water.

The impregnated product is maintained at room temperature for 4 hours and is subsequently dried at 120° C. for 24 hours. The dried product is then calcined, in a stream of dry air, at 750° C. and maintained at this temperature for 4 hours.

The weight composition of the catalyst is: 2.3% of Ga$_2$O$_3$, 0.7% of K$_2$O, 1.6% of SiO$_2$, Al$_2$O$_3$ the complement to 100.

The catalytic performances in the catalytic combustion of methane, effected as described above, are indicated in table 1, from which it can be deduced that the addition of gallium to the carrier develops the performances in the catalytic combustion.

EXAMPLE 2B

The catalyst of Example 2, after a week of aging in dehydrogenation cycles, is tested again in the catalytic combustion of methane, under the same operating conditions described above.

The results, indicated in Table 1, show a very limited drop in the performances.

EXAMPLE 3A

Catalyst Based on Gallium Promoted with Platinum 150 g of microspheroidal alumina prepared as described in Example 1 are impregnated, by means of the "incipient wetness" procedure, with 35 ml of an aqueous solution containing 24.5 g of a solution of $Ga(NO_3)_3$ (10.71% by weight of Ga), 14.3 g of a solution of $KNO_3$ (6.445% by weight of K), 1.07 g of a solution of $Pt(NO_3)_2$ at 1.45% of Pt, the remaining consisting of deionized water.

The impregnated product is dried and calcined as in the previous example.

The weight composition of the catalyst is: 2.3% of $Ga_2O_3$, 0.7% of $K_2O$, 100 ppm of Pt, 1.6% of $SiO_2$, $Al_2O_3$ the complement to 100.

The catalytic performances in the catalytic combustion of methane, effected as described above, are indicated in Table 1.

A significant improvement in the catalytic performances can be observed, due to the presence of platinum.

EXAMPLE 3B

The same formulate as Example 3A, at the end of the catalytic combustion test, is tested in the dehydrogenation of a stream of ethylbenzene and ethane to give styrene and ethylene. Table 2 indicates the results of the catalytic performances.

EXAMPLE 3C

The catalyst of Example 3B, after a week of aging in dehydrogenation cycles, is tested again in the catalytic combustion of methane, under the same operating conditions described above.

The results, indicated in Table 1, show that the platinum component loses its capacity of promoting combustion over a period of time.

EXAMPLE 4A

Manganese 150 g of microspheroidal alumina prepared as described in Example 1 are impregnated as above with a solution consisting of 24.5 g of a solution of $Ga(NO_3)_3$ (10.71% of Ga), 14.3 g of a solution of $KNO_3$ (6.445% of K), 1.61 g of a solution of $Mn(NO_3)_3$ at 14.45% of Mn, the remaining consisting of deionized water.

The impregnated product is dried and calcined as in the previous example.

The weight composition of the catalyst is: 2.3% of $Ga_2O_3$, 0.7% of $K_2O$, 0.2% of Mn (as $Mn_2O_3$), 1.6% of $SiO_2$, $Al_2O_3$ the complement to 100.

The catalytic performances in the catalytic combustion of methane, effected as described above, are indicated in Table 1. The results indicate that manganese, like platinum, also acts as combustion promoter.

EXAMPLE 4B

The same formulate as Example 4, at the end of the catalytic combustion test, is tested in the dehydrogenation of a stream of ethylbenzene and ethane to give styrene and ethylene. Table 2 indicates the results of the catalytic performances.

EXAMPLE 4C

The catalyst of Example 4B, after a week of aging in dehydrogenation cycles, is tested again in the catalytic combustion of methane, under the same operating conditions as Example 4.

The results, indicated in Table 1, show that the manganese component has a better stability in its activity as combustion promoter, over a period of time.

EXAMPLE 5

Manganese and Platinum 150 g of microspheroidal alumina prepared as described in Example 1 are impregnated with a solution consisting of 24.09 g of a solution of $Ga(NO_3)_3$ (10.93% of Ga), 14.4 g of a solution of $KNO_3$ (6.445% of K), 5.33 g of a solution of $Mn(NO_3)_3$ at 4.37% of Mn, 1.07 g of a solution of $Pt(NO_3)_2$ at 1.45% of Pt.

The impregnated product is dried and calcined as in the previous example.

The weight composition of the catalyst is: 2.3% of $Ga_2O_3$, 0.7% of $K_2O$, 100 ppm of Pt, 0.2% of Mn (as $Mn_2O_3$), 1.6% of $SiO_2$, $Al_2O_3$ the complement to 100.

The formulate is tested in the catalytic combustion reaction, giving the results indicated in Table 1. It can be deduced that the combination of platinum/manganese is also active in catalytic combustion.

EXAMPLE 6

Composite Mixture 100 g of microspheroidal alumina, prepared as described in Example 1, are impregnated with 24 cc of an aqueous solution containing 10.11 g of a solution of $KNO_3$ (6.445% of K), and 25.57 g of $Mn(NO_3)_3.4H_2O$. The impregnated product is then treated as described in Example 2.

The weight composition of the catalyst is: 0.8% of $K_2O$, 7.8% of Mn (as $Mn_2O_3$), 1.5% of $SiO_2$, $Al_2O_3$ the complement to 100.

3.5 g of this formulate are added to 122 g of the formulate of Example 2. The composite mixture has a composition similar to that of Example 4, i.e. 2.2% of $Ga_2O_3$, 0.2% of Mn (as $Mn_2O_3$), 0.72% of $K_2O$, the remainder consisting of the carrier.

This mixture is tested in the catalytic combustion of methane and the results are indicated in Table 1.

It can be deduced that the addition of manganese, both as co-impregnated product and as a composite mixture improves the catalytic combustion.

EXAMPLE 7

Comparative—Sample with a High Platinum Content 150 g of microspheroidal alumina prepared as described in Example 1 are impregnated as above with a solution consisting of 24.09 g of a solution of $Ga(NO_3)_3$ (10.93% of Ga), 14.3 g of a solution of $KNO_3$ (6.445% of K), 10.7 g of a solution of $Pt(NO_3)_2$ at 1.45% of Pt, 1.6 g of a solution of $Mn(NO_3)_3$ at 14.45% of Mn.

The impregnated product is dried and calcined as in the previous example.

The weight composition of the catalyst is: 2.3% of $Ga_2O_3$, 0.7% of $K_2O$, 1000 ppm of Pt, 0.2% of Mn (as $Mn_2O_3$), 1.6% of $SiO_2$, $Al_2O_3$ the complement to 100.

The formulate tested in the dehydrogenation of a mixture of Ethylbenzene/Ethane gives the results indicated in Table 2. It can be deduced that even if the high platinum contents can on the one hand further promote the catalytic combustion, on the other, they lower the performances during the dehydrogenation.

EXAMPLE 8

Test with a Varying Composition 150 g of microspheroidal alumina prepared as described in Example 1 are impregnated as above with a solution consisting of 10.228 g of $Ga(NO_3)_3.H_2O$ (25.8% of Ga), 2.445 g of $KNO_3$, 2.123 g of $Mn(NO_3)_3.4H_2O$, 0.031 g of $Pt(HCO_3)_2(NH_3)_4$, the remainder consisting of deionized water.

The impregnated product is dried and calcined as in the previous example.

The weight composition of the catalyst is: 2.3% of $Ga_2O_3$, 0.7% of $K_2O$, 70 ppm of Pt, 0.4% of Mn (as $Mn_2O_3$), 1.6% of $SiO_2$, $Al_2O_3$ the complement to 100.

The formulate is tested in the catalytic combustion reaction and gives the results indicated in Table 1. It can be deduced that the increased manganese content has further improved the catalytic properties in the catalytic combustion.

EXAMPLE 8B

The same formulate as Example 8A is tested in the dehydrogenation of ethylbenzene in the presence of ethane. The results are indicated in Table 2.

EXAMPLE 8C

The same formulate as Example 8A is tested in the dehydrogenation of ethylbenzene in the presence of nitrogen. The results are indicated in Table 2.

EXAMPLE 8D

The same formulate as Example 8A, after a total running time of 450 hours in dehydrogenation, is tested again in the catalytic combustion of methane, under the same operating conditions as Example 8A. The results, indicated in Table 1, confirm the stability of the formulate over a period of time.

TABLE 1

| EXAMPLE | Reaction Time (°C.) | GHSV (Nl/lcat/h) 200 | 400 | 600 |
|---|---|---|---|---|
| 1 | 620 | 69-7 | 48.5 | 39.7 |
|  | 640 |  | 84.5 | 61.8 | 50.9 |
|  | 650 | 88.8 | 67.3 | 57.0 |
| 2A | 620 | 91.9 | 76.0 | 65.6 |
|  | 640 | 95.8 | 84.2 | 74.8 |
|  | 650 | 97.9 | 87.9 | 79.7 |
| 2B | 620 | 90.8 | 73.4 | 62.7 |
|  | 640 | 95.4 | 83.6 | 74.0 |
|  | 650 | 97.2 | 87.2 | 78.7 |
| 3A | 640 | 98.9 | 91.7 | 81.5 |
|  | 670 | 99.9 | 97.5 | 90.4 |
| 3C | 620 | 91.2 | 71.9 | 59.3 |
|  | 640 | 95.7 | 84.3 | 73.9 |
|  | 650 | 97.2 | 87.3 | 77.9 |
| 4A | 620 | 98.5 | 87.1 | 78.4 |
|  | 640 | 99.3 | 92.5 | 85.5 |
|  | 650 | 99.5 | 94.6 | 88.9 |
| 4C | 620 | 97.4 | 83.1 | 72.9 |
|  | 640 | 99.2 | 90.4 | 82.7 |
|  | 650 | 99.0 | 93.5 | 86.6 |
|  | 670 | 99.9 |  |  |
| 5 | 620 | 98.7 | 90.2 | 81.9 |
|  | 650 | 99.7 | 97.2 | 92.7 |
| 6 | 620 | 93.6 | 80.3 | 70.0 |
|  | 640 | 97.9 | 88.0 | 81.3 |
|  | 650 | 99.0 | 91.7 | 84.7 |
| 8A | 600 | 97.6 | 89.1 | 90.8 |
|  | 620 | 99.4 | 95.6 |  |
| 8D | 600 | 97.8 | 89.2 | 81.5 |
|  | 620 | 99.7 | 94.8 | 90.1 |
|  | 650 | 99.0 |  |  |

TABLE 2

| Ex. | Feeding (V %) EB | N₂ | C₂H₆ | Press. (ata) | Reaction T (°C.) | GHSV (Nl/lcat/h) | HOS | Conv. (%) EB | C₂H₆ | Select. (M %) STY |
|---|---|---|---|---|---|---|---|---|---|---|
| 3B | 15 | — | 85 | 1.02 | 590 | 500 | 110 | 45.5 | 7.2 | 91.1 |
| 4B | 15 | — | 85 | 1.02 | 590 | 400 | 119 | 49.1 | 6.9 | 92.6 |
| 7 | 20 | — | 80 | 1.02 | 590 | 400 | 22 | 39.5 | 4.1 | 93.3 |
| 7 | 15 | — | 85 | 1.02 | 590 | 400 | 45 | 41.1 | 4.3 | 93.5 |
| 8B | 15 | — | 85 | 1.02 | 590 | 400 | 53 | 48.5 | 6.8 | 88.3 |
| 8C | 15 | 85 | — | 1.02 | 590 | 400 | 222 | 53.8 | — | 90.6 |

The invention claimed is:

1. A catalytic composition, comprising:
    a) a carrier consisting of alumina in delta phase, theta phase, or in a mixture of delta+theta, theta+alpha or delta+theta+alpha phase, modified with silica, and having a surface area lower than 150 m$^2$/g, determined by the BET method;
    b) 0.1-35% by weight of gallium, expressed as $Ga_2O_3$;
    c) 0.01-5% by weight of manganese, expressed as $Mn_2O_3$;
    d) 0-100 ppm by weight of platinum; and
    e) 0.05-4% by weight of an oxide of an alkali or alkaline-earth metal;
    wherein weight proportions are calculated relative to the total weight of the catalytic composition.

2. The catalytic composition according to claim 1, comprising:
    a) a carrier consisting of alumina in delta phase, theta phase, or in a mixture of delta+theta, theta+alpha or delta+theta+alpha phase, modified with silica, and having a surface area lower than 150 m$^2$/g;
    b) 0.2-3.8%; by weight of gallium, expressed as $Ga_2O_3$;
    c) 0.15-1.5% by weight of manganese, expressed as $Mn_2O_3$;
    d) 5-90 ppm by weight of platinum; and
    e) 0.1-3% by weight of the oxide of an alkali or alkaline earth metal; wherein weight proportions are calculated relative to the total weight of the catalytic composition.

3. The catalytic composition according to claim 1, wherein the alumina carrier is modified with 0.08-5% by weight of silica.

4. The catalytic composition according to claim 1, wherein the alkali or alkaline-earth metal is potassium or magnesium.

5. A process for the catalytic dehydrogenation of alkylaromatic hydrocarbons optionally mixed with ethane which comprises:
    A) dehydrogenating a hydrocarbon stream, optionally mixed with an inert gas, in a fluid bed reactor in the presence of a catalytic composition according to claim 1, at a temperature ranging from 400 to 650° C, at a total pressure ranging from 0.1 to 3 ata and with a GHSV ranging from 50 to 10,000 Nl/h·l$_{cat}$; and
    B) regenerating and heating the catalyst, by catalytic combustion, in a fluid bed regenerator at a temperature higher than 500° C.

6. The process according to claim 5, wherein the alkylaromatic hydrocarbon is ethylbenzene.

7. The process according to claim 5, wherein the inert gas is selected from the group consisting of nitrogen, methane, hydrogen, carbon dioxide, noble gases, and mixtures thereof.

8. The process according to claim 7, wherein the inert gas is selected from the group consisting of nitrogen, methane, and mixtures thereof.

9. The process according to claim 5, wherein the volume ratio of inert gas/hydrocarbon stream ranges from 1 to 10.

10. The process according to claim 9, wherein the volume of inert gas/hydrocarbon stream ratio ranges from 2 to 6.

11. The process according to claim 5, wherein said dehydrogenating conducted
    at a temperature ranging from 450 to 650° C.,
    at atmospheric pressure or a slightly higher value,
    at a GHSV ranging from 100 to 1,000 Nl/h·lat$_{cat}$, and
    with residence times of the catalyst ranging from 5 to 30 minutes.

12. The process according to claim 11, wherein the GHSV ranges from 150 to 400 Nl/h·l$_{cat}$, and the residence times of the catalyst ranges from 10 to 15 minutes.

13. The process according to claim 5, wherein said regenerating of the catalyst is conducted with air, oxygen or air diluted in nitrogen
    whereas said heating is conducted with methane, a fuel gas or by-products of the dehydrogenation reaction,
    wherein said regenerating is conducted at a higher temperature with respect to the dehydrogenation temperature, at atmospheric pressure or a slightly higher value, a GHSV ranging from 100 to 1,000 Nl/h·l$_{cat}$ and with a residence time of the catalyst ranging from 5 to 120 minutes.

14. The process according to claim 13, wherein the regeneration temperature ranges from 500 to 700° C and the residence time ranges from 20 to 40 minutes.

15. The process according to claim 5, wherein, in step (A), a mixture of ethylbenzene-ethane is fed to the reactor to obtain the contemporaneous dehydrogenation thereof, using the ethane in a mixture with benzene to give the corresponding alkylaromatic.

16. A catalytic composition, comprising:
    i) 70-99.5% by weight of a first active phase consisting essentially of:
        a solid carrier based on alumina in delta phase, theta phase, or in a mixture of delta+theta, theta+alpha or delta+theta+alpha phase, modified with silica, and having a surface area lower than 150 m$^2$/g, determined by the BET method,
        0.1-35% by weight of gallium, expressed as $Ga_2O_3$, and
        0.05-4% by weight of an oxide of an alkali or alkaline-earth metal supported on alumina; and
    ii) 0.5-30% by weight of a second active phase consisting essentially of:
        a solid carrier based on alumina in delta phase, theta phase, or in a mixture of delta+theta, theta+alpha or delta+theta+alpha phase, modified with silica, and having a surface area lower than 150 m$^2$/g, determined by the BET method,
        0.1-10% by weight of modified with manganese, expressed as $Mn_2O_3$,
        0-1000 ppm by weight of platinum, and
        0.025-3.95% by weight of an oxide of an alkali or alkaline-earth metal supported on alumina, wherein i) and ii) are present as a mixture.

17. The catalytic composition according to claim 16, wherein
    the weight of gallium ranges from 0.2 to 3.8% by weight,
    the weight of manganese ranges from 0.15 to 1.5% by weight,
    the weight of platinum ranges from 5 to 50 ppm by weight, and
    the total weight of the alkali or alkaline-earth metal oxide ranges from 0.1-3% by weight.

18. A process for the preparation of the catalytic composition according to claim 16, which comprises: mixing particles of alumina classified as belonging to group A according to Geldart (Gas Fluidization Technology, D. Geldart, John Wiley & Sons).

19. A catalytic composition, comprising:
    i) 70-99.5% by weight of a first active phase consisting essentially of:
        a solid carrier based on alumina in delta phase, theta phase, or in a mixture of delta+theta, theta+alpha or delta+theta+alpha phase, modified with silica, and having a surface area lower than 150 m$^2$/g, determined by the BET method,
        0.1-35% by weight of gallium, expressed as $Ga_2O_3$, and 0.025-2% by weight of an oxide of an alkali or alkaline-earth metal supported on alumina;

ii) 0-30% by weight of a second active phase consisting essentially of:
- a solid carrier based on alumina in delta phase, theta phase, or in a mixture of delta+theta, theta+alpha or delta+theta+alpha phase, modified with silica, and having a surface area lower than 150 m²/g, determined by the BET method,
- 0.1-10% by weight of manganese, expressed as $Mn_2O_3$, and
- 0.025-3.95% by weight of an oxide of an alkali or alkaline-earth metal supported on alumina; and iii) 0-30% by weight of a third active phase consisting essentially of:
- a solid carrier based on alumina in delta phase, theta phase, or in a mixture of delta+theta, theta+alpha or delta+theta+alpha phase, modified with silica, and having a surface area lower than 150 m²/g, determined by the BET method,
- 5-1000 ppm by weight of platinum, and
- 0.025-3.95% by weight of an oxide of an alkali or alkaline-earth metal supported on alumina, wherein i), ii), and iii) are present as a mixture.

20. The catalytic composition according to claim 19, wherein
- the weight of gallium ranges from 0.2 to 3.8% by weight,
- the weight of manganese ranges from 0.15-1.5% by weight,
- the weight of platinum ranges from 5 to 50 ppm by weight, and the total weight of the alkali or alkaline-earth metal oxide ranges from 0.1-3% by weight.

21. A process for the preparation of the catalytic composition according to claim 1, which comprises:
- preparing one or more solutions of components to be supported;
- dispersing the solutions on an alumina carrier impregnated with silica;
- drying the impregnated alumina carrier to produce a dried carrier; and
- calcining the dried carrier at least once at a temperature ranging from 500 to 900° C.

22. The process according to claim 21, wherein the impregnated alumina carrier is in the form of particles classified as belonging to group A according to Geldart.

* * * * *